United States Patent [19]
Steffen

[11] Patent Number: 5,508,396
[45] Date of Patent: Apr. 16, 1996

[54] PROCESS FOR PREPARING N-ALKYLLACTAMS

[75] Inventor: Klaus-Dieter Steffen, Hennef, Germany

[73] Assignee: Huels Aktiengesellschaft, Marl, Germany

[21] Appl. No.: 421,237

[22] Filed: Apr. 13, 1995

[30] Foreign Application Priority Data

Jul. 6, 1994 [DE] Germany ............... 44 23 603.4

[51] Int. Cl.$^6$ .................................... C07D 223/06
[52] U.S. Cl. .................... 540/451; 540/533; 548/443; 548/552
[58] Field of Search ................ 548/543, 552; 540/451, 533

[56] References Cited

U.S. PATENT DOCUMENTS

| | | | |
|---|---|---|---|
| 3,588,248 | 6/1971 | Freund et al. | 355/74 |
| 3,865,814 | 2/1975 | Lüssi et al. | 260/239.3 |
| 4,310,948 | 1/1982 | Röck et al. | 16/335 |
| 4,380,162 | 4/1983 | Woolfson | 70/276 |

*Primary Examiner*—Joseph K. McKane
*Attorney, Agent, or Firm*—Oblon, Spivak, McClelland, Maier & Neustadt

[57] ABSTRACT

A process for preparing an N-alkyllactam, comprising the steps of:

(a) reacting a lactam with an alkali metal alkoxide at 130°–170° C. and removing the alcohol formed by distillation;

(b) reacting the product from step (a), if desired in a mixture with the product from step (e), with an alkyl halide in a solvent which is
   (i) an ethylene glycol dialkyl ether of the formula R—O—(CH$_2$—CH$_2$—O)$_m$R, where R in C$_1$–C$_4$-alkyl and m is 1–8,
   (ii) the N-alkyllactam to be prepared or
   (iii) a mixture of (i) and (ii), to obtain crude N-alkyllactam or an alkali metal salt;

(c) separating the alkali metal salt from the crude N-alkyllactam;

(d) subjecting the N-alkyllactam crude product to high-purity distillation after addition of a sufficient amount of alkali metal alkoxide to convert any unreacted lactam to a salt; and (e) recycling the bottom product of the distillation in step (d) in step (e) into step (b), is environmentally friendly and affords the desired N-alkyllactam in high yield and high purity.

11 Claims, No Drawings

PROCESS FOR PREPARING N-ALKYLLACTAMS

BACKGROUND OF THE INVENTION

1. Field of the Invention

The present invention relates to a process for preparing N-alkyllactams from lactams and alkyl halides.

2. Discussion of the Background

N-alkyllactams are compounds which are known from the literature (Houben-Weyl, Methoden der Organ. Chemie (Methods of Organic Chemistry), G. Thieme Verlag Stuttgart, Vol. XI/2, p. 568).

The most frequently used preparation method is to react a lactam with metallic sodium or NaH in xylene or benzene and to further react the resulting product with an alkyl halide or alkyl sulfate to give the N-alkyllactam. Thus, A. P. Swain et al. (*J. Org. Chemistry*, vol. 18, p. 1087 (1953)) prepared N-hexadecylcaprolactam and other N-alkylcaprolactams in a reported yield of 62% by boiling in xylene for 40 hours. In this manner, C. S. Marvel and W. W. Moyer (*J. Org. Chemistry*, vol. 22, p. 1065 (1957)) achieved yields of 63–78% for various N-alkylcaprolactams. By exactly the same method, T. Duong et al. (*Austr. J. Chem.*, vol. 29, p. 2651 (1976)) prepared seven further N-alkyllactams using NaH in benzene as the condensation medium.

However, the handling of metallic sodium or NaH and the use of carcinogenic solvents is associated with higher risks. Moreover, the reported yields of these methods are not yet satisfactory.

The condensation of lactams with alkyl halides in aqueous systems using NaOH with phase transfer catalysis has also been described. J. Palecek and J. Kuthan (*Z. Chemie*, vol. 17, p. 260 (1977)) report that the yields decrease with increasing ring size of the lactam and increasing C number of the alkyl bromide; the yields obtained are 15–73%. U.S. Pat. No. 4,380,162 reports that when using the PT catalyst tetrabutylammonium hydrogen sulfate reaction times of 114 hours are necessary for achieving yields of >90% of N-dodecylcaprolactam. Such long reaction times are uneconomical, traces of sulfur frequently interfere in the subsequent reactions, and the disposal of the aqueous chlorocarbon-containing phase also presents a problem.

Other preparation methods include the condensation of lactones with alkylamines at elevated temperatures of about 275° C. and pressures of up to 33 bar with elimination of water (PCT Int. Appl. WO 8800 184) or the cyclization of ω-alkylaminocarboxylic acids at about 230° C. with elimination of $H_2O$ (DE-A 3,735,904). The ring closure of ω-dialkylaminocarboxylic acids with phosphoric acid chlorides at elevated temperatures has also been described (U.S. Pat. Nos. 4,310,948 and 3,588,248). All these methods comprise several complicated synthetic steps.

Thus, there remains a need for a process of preparing N-alkyllactams which is environmentally friendly and affords the desired N-alkyllactam in high yield and high purity.

SUMMARY OF THE INVENTION

Accordingly, it is one object of the present invention to provide a novel process for preparing N-alkyllactams which is environmentally friendly.

It is another object of the present invention to provide a novel process for preparing N-alkyllactams which affords the desired N-alkyllactam in high yield.

It is another object of the present invention to provide a novel process for preparing N-alkyllactams which affords the desired N-alkyllactam in high purity.

These and other objects, which will become apparent during the following detailed description, have been achieved by the inventor's discovery that a process, in which: the lactam and alkyl halide are reused as starting materials; the condensation is carried out after the addition of a sodium alkoxide or potassium alkoxide and removal of the alcohol by distillation; and the solvent used is a diethylene glycol dialkyl ether or the N-alkyllactam to be prepared itself, is environmentally friendly and affords the desired N-alkyllactam in high yield and high purity. Thus, the present process gives yields of ≧90% of theory. The present process can be carried out without superatmospheric pressure or at only a slight superatmospheric pressure and at temperatures of 130° C.–170° C. Furthermore, the present process is gentle on the environment since the alcohol of the alkali metal alkoxide is condensed and recycled, the alkali metal halide is isolated but no waste water is formed.

In particular, the present invention provides a process for preparing an N-alkyllactam, comprising the steps of:

(a) reacting a lactam with an alkali metal alkoxide at 130°–170° C., to form an alcohol and a lactam salt and removing the alcohol by distillation;

(b) reacting the lactam salt from step (a), if desired in a mixture with the bottom product from step (e), with an alkyl halide in a solvent which is:
  (i) an ethylene glycol dialkyl ether of the formula $R—O—(CH_2—CH_2—O)_m R$, where R is $C_1$–$C_4$-alkyl and m is 1–8,
  (ii) the N-alkyllactam to be prepared, or
  (iii) a mixture of (i) and (ii), to obtain crude N-alkyllactam and an alkali metal salt;

(c) separating the alkali metal salt from the crude N-alkyllactam, (d) subjecting the crude N-alkyllactam product to high-purity distillation after addition of a sufficient amount of alkali metal alkoxide to convert any unreacted lactam present in said crude N-alkyllactam, to a salt; and (e) recycling the bottom product of distillation from step (d) into step (b).

DETAILED DESCRIPTION OF THE PREFERRED EMBODIMENTS

Suitable lactam starting materials for use in the present invention include those in which the lactam functional group contains a hydrogen atom bonded to the nitrogen atom. Moreover, suitable starting material lactams include those in which the lactam functional group is contained in a ring of from 4 to 15 atoms in size, preferably from 5 to 13 atoms in size. One or more of the carbon atoms in the lactam ring may be substituted with one or more substituents selected from the group consisting of $C_{1-4}$-alkyl, phenyl, and $C_{1-4}$-alkoxyl. Specific examples of lactams useful as starting materials in the present process include ε-caprolactam, pyrrolidone (butyrolactam), and ε-laurolactam.

The alkali metal alkoxides used are usually the simple sodium methoxide or potassium methoxide as an approximately 30 wt % strength methanolic solution. However, it is also possible to use the alkoxide in pulverulent form or in a solution of greater or lesser strength. Sodium and potassium ethoxides may also be used. Preference is given to the potassium alkoxides since the potassium salts usually exhibit better solubility than the corresponding sodium salts. The alkali metal alkoxides are reacted with the lactam to be alkylated. In order to complete salt formation (sodium or potassium lactam) and to avoid the formation of ether byproducts, the methanol has to be distilled off entirely, which is suitably achieved by applying a slight vacuum toward the end of the reaction. This salt formation proceeds very selectively at temperatures of 140°–165° C., despite the description in the literature (B. Vollmert, Gundriss der Makromolekularen Chemie (Principles of Macromolecular Chemistry), Springer-Verlag, p. 154) that sodium methoxide is a highly useful initiator for rapid polymerization of pyrrolidone and other lactams. The alcohol may be distilled from the reaction mixture as the alkoxide is being added. Typically, the addition of alkoxide and removal of alcohol can be completed within two hours, preferably within one hour.

The molar ratio of alkoxide to starting lactam is suitably 0.95:1 to 1.15:1, preferably 1:1 to 1.1:1, most preferably about 1.05:1.

Suitable alkyl halides for use in the present process include the straight-chain or branched $C_{1-14}$-alkyl halides (chloride, bromide or iodide). Specific examples include methyl chloride, ethyl chloride, propyl chloride, pentyl chloride, n-octyl chloride, n-butyl chloride, and n-dodecyl chloride. The molar ratio of alkyl halide to starting lactam is suitably 0.95:1 to 1.15:1, preferably 1:1 to 1.1:1, more preferably about 1.05.1.

The alkyl halide, in general the simple alkyl chloride, is metered in at these temperatures (130°–170° C.) in a slightly exothermic reaction. Depending on the boiling point of this alkyl halide, the reaction is carried out without superatmospheric pressure or under a slight superatmospheric pressure.

In the reaction of the lactam salt with the alkyl halide, two different types of solvents can be used. The ethylene glycol dialkyl ethers of the general formula $RO-(CH_2-CH_2-O)_mR$ ($R=C_1-C_4$-alkyl, m=1–8) have a very favorable effect on the course of the reaction owing to the good solubility of the alkali metal lactam salts and the acceleration of the reaction, resulting in a shortening of the reaction time. Owing to its favorable boiling point of about 160° C., diethylene glycol dimethyl ether is preferred, although the mono and triethylene glycol derivatives can also be used, depending on the boiling point of the target product. The reaction between the alkyl halide and the alkali metal lactam salt is typically complete after a time of ten hours, more typically within 2–8 hours. The KCl or NaCl formed in these solvents can usually be readily separated from the crude N-alkyllactam, for example, by filtration. After being washed with alcohol, for example methanol, this salt can be recycled into the electrolysis cycle and can then be converted into alkali metal alkoxide.

If it is desired to avoid foreign chemicals, the solvent used in this reaction can also be the N-alkyllactam itself (target product) prepared in a first batch, for example in xylene or toluene as the solvent. If an N-alkyllactam is used as the solvent, it is often recommended that the reaction mixture, in order to separate the alkali metal halide, be distilled as a whole in a short-path distillation apparatus. The alkali metal halide is then discharged in dry form and can, if it is pure enough, also be re-introduced into the electrolysis cycle.

To remove any incompletely reacted residual lactam present in the crude N-alkyllactam product, it is advantageous to add a stoichiometric amount of alkali metal alkoxide to this crude product prior to high-purity distillation. The amount of residual starting material lactam present in the crude N-alkyllactam can be determined by any conventional technique capable of measuring the amount of starting lactam present in such a mixture, such as high performance liquid chromatography (HPLC) or gas chromatography (GC). The use of GC is preferred. The molar ratio of alkoxide to residual starting lactam is suitably 0.99:1 to 1.10:1, preferably 1.00:1 to 1.05:1, more preferably about 1:1. In this manner, the residual lactam in retained in the bottom product of the distillation as the sodium salt and can as such also be re-introduced into subsequent batches. The high-purity distillation may be, e.g., column distillation, spinning band distillation, etc.

The N-alkyllactams prepared by the present process are used as selective solvents, especially in extractions, as plasticizers, as starting materials for pharmaceutical products and in combination with pesticides.

Other features of the invention will become apparent in the course of the following descriptions of exemplary embodiments which are given for illustration of the invention and are not intended to be limiting thereof.

EXAMPLES

Example 1

N-n-Octylcaprolactam (NOC)

a) In a liter four-neck flask equipped with stirrer, thermometer, dropping funnel, and distillation head, 114 g of ε-caprolactam (1.0 mol) is heated in 450 g of xylene to about 130° C., and 90 g (0.5 mol) of a 30 wt. % strength sodium methoxide-methanol solution is then added dropwise while continuously distilling methanol. At the end, a slight vacuum of about 800 mbar is applied, the mixture is heated to about 140° C., and all the methanol is removed. At this temperature, the first portion of 75 g of n-octyl chloride (0.5 mol) is metered in, and the reaction is brought to completion over a period of three hours.

The second amount of 99 g (0.55 mol) of 30 wt. % strength sodium methoxide-methanol solution is likewise metered in at about 140° C., and the methanol is again distilled completely. This is followed by addition of the second portion of 81 g of n-octyl chloride (0.55 mol) at about 140° C. over a period of 30 minutes. The reaction time is 4–5 hours. The reaction mixture is then cooled to 70°–80° C., and the precipitated NaCl is removed by filtration and washed with methanol (amount of NaCl: 58 g). The filtrate is subjected to fractional distillation under reduced pressure gradually decreasing from 300 mbar to 15 mbar, and the methanol and the xylene are distilled up to a flask temperature of 140° C. An oil pump vacuum is then applied, and NOC is distilled at a temperature of 120° C. and a pressure of 0.5 mbar.

Amount of NOC distillate: 215 g; purity: 96% of NOC, 2.5% of caprolactam (GC).

Yield: 91.5% of theory.

b) In the same apparatus as described in a), the 215 g of crude NOC product is heated together with 57 g of caprolactam (0.5 mol) to 145°–150° C., and 95 g of 30 wt. % strength sodium methoxide-methanol solution (0.525 mol) is metered in while simultaneously distilling methanol. The residual methanol is removed by applying vacuum.

78 g of n-octyl chloride (0.525 mol) is then metered in at a flask temperature of 150°–160° C. over a period of 30 minutes and allowed to react for a time of 4–5 hours.

All the NOC is then distilled from the NaCl at a vacuum of 0.1–1 mbar and a still temperature of 120°–130° C. For high-purity distillation, see Example 4. Weight: 322 g having a gas chromatography (GC) purity of 96.5%. Yield: (310.7 g−206.4 g)=104.3 g of NOC, which corresponds to 92.6% of theory.

Example 2

N-n-Octylcaprolactam (NOC)

In the apparatus as described in Example 1, 500 ml of diglycol dimethyl ether and 113.2 g of ε-caprolactam are heated to 145°–150° C., and 230 g of 32 wt. % strength potassium methoxide-methanol solution (1.05 mol) is added dropwise at this temperature over a period of one hour while continuously distilling methanol. The solution always remains clear. The residual methanol has to be removed by applying vacuum (about 700 mbar).

156 g of n-octyl chloride (1.05 mol) is then metered in likewise at 145°–150° C. over a period of one hour, and the reaction is completed over a period of another 5 hours.

After being cooled to 40°–50° C., the reaction mixture is filtered, and the KCl is washed with the solvent and methanol and dried to give 76 g of KCl. The filtrate is column distilled into the individual fractions, methanol and diglycol dimethyl ether, under a gradually improving vacuum, and the NOC is distilled from all high-boilers at a vacuum of 1 mbar.

Crude NOC distillate: 218 g having a GC purity of 91.31% of NOC, 3.92% of caprolactam, which corresponds to a yield of 88.3% of theory or 95.5% if the unreacted caprolactam is recycled. For high-purity distillation, see Example 4.

Example 3

N-n-octylcaprolactam (NOC)

As described in Example 2, 113.2 g of ε-caprolactam (1.0 mol) is dissolved in 500 ml of diglycol dimethyl ether, and 188 g of a 30,16 wt. % strength sodium methoxide-methanol solution (1.05 mol) is metered in at 150°–160° C. while continuously distilling methanol. The sodium salt of caprolactam precipitates in part.

Metered addition of 156 g of n-octyl chloride (1.05 mol) is effected over a period of 40 minutes, and the reaction is continued for an additional 8 hours. After the NaCl (59 g) has been removed by filtration, the crude product is worked up by distillation.

This gives an NOC main fraction of 212 g having a GC purity of 94.5% of NOC and 2.86% of caprolactam, which corresponds to a yield of 88.9% or 93.9% if the unreacted caprolactam is taken into account. For high-purity distillation, see Example 4.

Example 4

High-purity distillation of N-n-octylcaprolactam

Several batches from the previous examples were collected (about 95% of NOC, about 3% of caprolactam), a stoichiometric amount of NaOCH$_3$ based on caprolactam is added, and the mixture is subjected to high-purity vacuum distillation in a short-column distillation apparatus. After a forerun, the pure product distills at a temperature of 120° C. and a pressure of 0.5 mbar. Purity: 98.7% of NOC.

The bottom product of distillation consisting mainly of sodium caprolactam is re-introduced into the next batch.

Example 5

N-Butylcaprolactam (NBC)

a) In the apparatus as described in Example 1, 114 g of ε-caprolactam (1.0 mol) is dissolved in 450 g of xylene by heating, and 90 g of a 30.16 wt. % strength sodium methoxide-methanol solution (0.5 mol) is metered in at 140° C. over a period of one hour. The methanol is distilled completely. 46 g of n-butyl chloride (0.5 mol) is metered in likewise at 140° C. over a period of 30 minutes, and the mixture is allowed to continue reacting for about 3 hours.

n-Butylation of the second half using 98 g of NaOCH$_3$ solution (0.55 mol) and 51 g of n-butyl chloride (0.55 mol) is carried out in the same manner.

After cooling, 50 ml of methanol is added to the reaction mixture, and the NaCl is removed by filtration, washed, and dried (61 g of NaCl). The filtrate is vacuum-distilled through a short column. After removing a forerun of methanol and xylene, N-butylcaprolactam is distilled at a temperature of 90° C. and a pressure of 0.5 mbar. Weight: 151 g. GC purity: 96.4% of NBC, 3.5% of caprolactam. Yield: 86% or 89.5% of theory if caprolactam is recycled.

b) 113.2 g of fresh caprolactam (1.0 mol) is dissolved in 250 g of crude distillate containing 3.4% of caprolactam (8.5 g of caprolactam prepared as in a), and the resulting mixture is heated to 150° C. 202 g of a 30.16 wt. % strength sodium methoxide-methanol solution (1.13 mol) is metered in at 140° C. over a period of one hour while distilling methanol. All the methanol is distilled by briefly applying vacuum. 104.5 g of n-butyl chloride (1.13 mol) is then metered in at 140° C. over a period of one hour. After allowing the mixture to continue reacting for 4 hours, the reaction mixture is subjected to an initial cooling, and all the NBC is distilled from the sodium chloride in vacuo; boiling point of NBC: 90° C./0.5 mbar. Weight: 406 g. GC Purity: 96.3% of NBC, 2.7% of caprolactam. Yield: 83.0% of theory or 91.2% if caprolactam is recycled. NBC can be redistilled through a column to give a product having a purity of about 99%.

Example 6

N-Dodecylcaprolactam (NDDC)

a) 230.5 g of a 31.98 wt. % strength potassium methoxide-methanol solution (1.05 mol) is added dropwise at 150° C. to a solution of 113.2 g of ε-caprolactam (1.0 mol) in 500 ml of diethylene glycol dimethyl ether. During the 75 minutes of metered addition, methanol is distilled. 215 g of n-dodecyl chloride (1.05 mol) is then metered into the clear solution at 155° C. over a period of 45 minutes, and the mixture is allowed to react for about 8 hours.

The still hot reaction mixture of about 50° C. is filtered, and the KCl removed by filtration is washed with methanol and dried (75 g of KCl). The filtrate is vacuum-distilled through a column. After removing methanol and diethylene glycol dimethyl ether, which are reused in subsequent batches, NDDC is distilled under a high vacuum. Boiling point: 165°–168° C./1 mbar. Weight: 258.4 g. Purity: 95.1% of NDDC, 3.7% of caprolactam. Yield: 87.3% of theory or 95.4% of theory after subtracting the unreacted caprolactam.

b) NDDC was prepared under identical conditions using 188 g of a 30.16 wt. % strength sodium methoxide-methanol solution (1.05 mol) to give very similar results. High-purity distillation:

The calculated stoichiometric amount of sodium methoxide corresponding to the caprolactam content of 3.7% is added, and NDDC is then distilled under a high vacuum. In this case, the purity of the distilled NDDC is ≧99%. The sodium caprolactam is added to the subsequent batch.

Example 7

N-n-Octylpyrrolidone (NOP; N-n-Octylbutyrolactam)

a) 230 g of a 31.98 wt. % strength potassium methoxide-methanol solution (1.05 mol) is added dropwise at about 155° C., while distilling methanol to a solution of 85.2 g of 2-pyrrolidone (butyrolactam, 1.0 mol) in 500 ml of diethylene glycol dimethyl ether. For complete removal of all the methanol, the clear solution is evacuated for a short period until reaching 500 mbar. 156 g of n-octyl chloride (1.05 mol) is then metered in likewise at 155° C. over a period of 20 minutes, and the reaction is brought to completion over a period of another 6 hours.

The KCl is removed by filtration, washed with methanol, and dried: 75 g. The filtrate is distilled through a column. After foreruns of methanol and diethylene glycol dimethyl ether, NOP distills over at 125° C./1 mbar. Weight: 192 g. Purity: 95.6%, 1.1% of pyrrolidone. Yield: 93.0% or 95.4% of theory if the unreacted pyrrolidone is taken into account.

Example 8

N-n-Octyllaurolactam (NOL, N-n-Octyldodecyllactam)

49.7 g of ε-laurolactam (0.25 mol) is dissolved in 250 ml of diethylene glycol dimethyl ether, and 57.6 g of a 31.98 wt. % strength potassium methoxide-methanol solution (0.2625 mol) is metered in at 160° C.

To remove the last residual methanol, vacuum is applied for about one hour. 39.0 g of n-octyl chloride is then metered in over a period of 30 minutes, and the mixture is allowed to react for about another 8 hours. The KCl is removed by filtration at 70° C., washed with methanol, and dried (19 g of KCl). First, methanol and other byproducts are distilled under a slight vacuum. A good oil pump vacuum is then applied, and the target product is distilled in a short-path distillation apparatus at a temperature of 170° C. and a pressure of 0.3 mbar as an oily liquid, after having removed a forerun containing about 20% (GC) of unreacted laurolactam.

GC purity of the main fraction: 98.95% of NOL, 0.5% of laurolactam.

This application is based on German Patent Application No. P 44 23 603.4 filed on Jul. 6, 1994, which is incorporated herein by reference.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A process for preparing an N-alkyllactam, comprising the steps of:

(a) reacting a lactam with an alkali metal alkoxide at 130°–170° C., to obtain an alcohol and a lactam salt, and removing said alcohol by distillation;

(b) reacting said lactam salt from step (a), if desired in a mixture with the bottom product from step (e), with an alkyl halide in a solvent selected from the group consisting of:

(i) an ethylene glycol dialkyl ether of the formula R—O—(CH$_2$—CH$_2$—O)$_m$R, where R is C$_1$–C$_4$-alkyl and m is 1–8, (ii) said N-alkyllactam, and iii) a mixture of (i) and (ii), to obtain crude N-alkyllactam and an alkali metal salt;

(c) separating said alkali metal salt from said crude N-alkyllactam;

(d) subjecting the crude N-alkyllactam product to high-purity distillation after addition of a sufficient amount of alkali metal alkoxide to convert any unreacted lactam in said crude N-alkyllactam to a salt; and (e) recycling the bottom product of said distillation in step (d) into step (b).

2. The process of claim 1, wherein said reacting of said lactam with said alkali metal alkoxide in said step (a) is carried out at a temperature of 140°–165° C.

3. The process of claim 1, wherein said removing of said alcohol in said step (a) is carried out during said reacting or after said reacting in step (a).

4. The process of claim 1, wherein said solvent in said reacting in said step (b) is diethylene glycol dimethyl ether.

5. The process of claim 1, wherein said solvent in said reacting in said step (b) is said N-alkyllactam.

6. The process of claim 1, wherein said alkali metal alkoxide is sodium methoxide or potassium methoxide.

7. The process of claim 1, wherein said alkylhalide is a straight-chain or branched C$_{1-14}$-alkyl halide.

8. The process of claim 1, wherein said alkyl halide is selected from the group consisting of n-octyl chloride, n-butyl chloride, and n-dodecyl chloride.

9. The process of claim 1, wherein said lactam has a ring size of 4 to 15 atoms with all of the carbon atoms in the ring being unsubstituted or one or more of the carbon atoms in the lactam ring being substituted with one or more substituents selected from the group consisting of C$_{1-14}$-alkyl, phenyl, and C$_{1-14}$-alkoxy.

10. The process of claim 1, wherein said lactam has a ring size of from 5 to 13 atoms with all of the carbon atoms in the ring being unsubstituted or one or more of the carbon atoms in the ring being substituted with one or more substituents selected from the group consisting of C$_{1-4}$-alkyl, phenyl, and C$_{1-4}$-alkoxy.

11. The process of claim 1, wherein said lactam is selected from the group consisting of ε-caprolactam, pyrrolidone, and ε-laurolactam.

* * * * *